United States Patent [19]

Spielmann et al.

[11] Patent Number: 4,590,295
[45] Date of Patent: May 20, 1986

[54] PROCESS FOR THE MANUFACTURE OF P-HYDROXYPHENYL-ACETIC ACID

[75] Inventors: Werner Spielmann, Kelkheim; Georg Schaeffer, Hofheim am Taunus, both of Fed. Rep. of Germany

[73] Assignee: Hoechst Aktiengesellschaft, Frankfurt, Fed. Rep. of Germany

[21] Appl. No.: 726,274

[22] Filed: Apr. 24, 1985

Related U.S. Application Data

[63] Continuation of Ser. No. 225,190, Jan. 15, 1981.

[30] Foreign Application Priority Data

Jan. 17, 1980 [DE] Fed. Rep. of Germany ....... 3001511

[51] Int. Cl.$^4$ .............................................. C07C 65/01
[52] U.S. Cl. .................................................... 562/478
[58] Field of Search ........................................ 562/478

[56] References Cited

FOREIGN PATENT DOCUMENTS 3825 5/1979 European Pat. Off. ............ 562/478

Primary Examiner—Paul J. Killos
Attorney, Agent, or Firm—Curtis, Morris & Safford

[57] ABSTRACT p-Hydroxyphenylacetic acid is prepared by reduction of p-hydroxymandelic acid with HI in the presence of red phosphorus. According to a preferred embodiment, the reaction is carried out in one vessel in which the mandelic acid is prepared in situ from phenol and glyoxylic acid.

4 Claims, No Drawings

PROCESS FOR THE MANUFACTURE OF P-HYDROXYPHENYL-ACETIC ACID

This application is a continuation of application Ser. No. 225,190, filed Jan. 15, 1981.

p-Hydroxyphenylacetic acid is a valuable intermediate in various fields, especially in the pharmaceutical sector, for example for the preparation of substances having an antibiotic effect (cf. U.S. Pat. No. 2,487,018), of β-blockers (cf. British Patant No. 1,285,038).

To manufacture p-hydroxyphenylacetic acid various methods are known. A recently disclosed method (European Offenlegungsschrift No. 3,825) uses o-chlorophenol and glyoxylic acid as starting compounds which are transformed into p-hydroxyphenylacetic acid in three stages as follows:

(a) o-chlorophenol is reacted with glyoxylic acid to give 3-chloro-4-hydroxymandelic acid, (b) 3-chloro-4-hydroxymandelic acid is reduced to 3-chloro-4-hydroxyphenylacetic acid, preferably with hydroiodic acid HI, in the presence of red phosphorus, and (c) the chlorine atom of 3-chloro-4-hydroxyphenylacetic acid is split off, preferably by catalytic hydrogenation in contact with a palladium catalyst.

The detour via 3-chloro-4-hydroxymandelic acid is used since it has been understood that p-hydroxymandelic acid (which does not carry further substituents) cannot be reduced "in simple manner" to p-hydroxyphenylacetic acid. By the expression "reduction in simple manner" is meant the preferred reduction with hydroiodic acid HI of the aforesaid European Offenlegungsschrift, which is also reported in text-books of organic chemistry as the standard method for the reduction of (unsubstituted) mandelic acid to give (unsubstituted) phenylacetic acid (cf. for example, Fieser & Fieser, Lehrbuch der organischen Chemie, Verlag Chemie GmbH, Weinheim/Bergstrasse, Federal Republik of Germany, pages 784–785 (1960)).

According to German Offenlegungsschrift No. 2,820,854, which has an earlier priority, the direct reduction of p-hydroxymandelic acid to give the desired p-hydroxyphenylacetic acid has also been successful in various "simple" ways. The reduction of p-hydroxymandelic acid to p-hydroxyphenylacetic acid according to the aforesaid German Offenlegungsschrift proceeds as follows:

(a) by catalytic hydrogenation in contact with a palladium catalyst in mineral acid, preferably hydrochloric acid, solution, (b) with hypophosphorous acid $H_3PO_2$ or a salt thereof, or (c) with a chromium(II) salt, prepared in situ by reduction of a chromium(III) salt with Zn/acid.

In Example 1 of the German Offenlegungsschrift describing method (a) (catalytic hydrogenation), a yield of p-hydroxyphenylacetic acid of 85% of the theoretical is indicated, but, as ascertained by our own experiments, the drawback of this method resides in the fact that strongly colored (red) p-hydroxyphenylacetic acid having a melting point of 145° to 147° C. (theoretical melting point 150° C.) is obtained. In addition, the amount of salt formed as a result of the necessary neutralization of the mineral acid used should not be ignored.

As described in Example 3, method (b), i.e. reduction with $H_3PO_2$ or its salts, gives a yield of 67% of the theoretical which is not very satisfactory.

In spite of the high yield of p-hydroxyphenylacetic acid of 97% of the theoretical, method (c) i.e. the reduction with chromium(II) salt or chromium(III) salt-Zn/acid, as described in Example 2, has the disadvantage that a considerable amount of metal salts is required and obtained, which pollute the sewage.

The German Offenlegungsschrift is silent about the reduction of p-hydroxymandelic acid with hydroiodic acid HI to give p-hydroxyphenylacetic acid in a manner analogous to the reduction of (unsubstituted) mandelic acid to give (unsubstituted) phenylacetic acid. Hence, it is quite obvious that the authors of the said patent were of the opinion that the method of reduction by means of HI could not be used for p-hydroxymandelic acid. As regards this method, the prejudice created by European Offenlegungsschrift No. 3,852 is not overcome by German Offenlegungsschrift No. 2,820,854. On the contrary, it rather confirms the above prejudice as it uses, from among the various direct reduction methods, the relatively less favorable Cr(II) salt method instead of the more favorable HI method.

According to the state of the art it could, therefore, be assumed that the reduction of p-hydroxymandelic acid to give p-hydroxyphenylacetic acid by means of hydroiodic acid HI would be impossible and, in addition, that the "one vessel" reaction known from the heterocyclic series for the manufacture of pyrrylacetic acid from pyrrole or pyrrole derivatives, glyoxylic acid and HI, in which corresponding pyrrylhydroxyacetic acids are probably formed as intermediates could not be transferred to the manufacture of p-hydroxyphenylacetic acid. The "one vessel" reaction in the pyrrole series is described in Canad.J.Chem. 48, 139–143 (1970).

It can be illustrated by the following equation

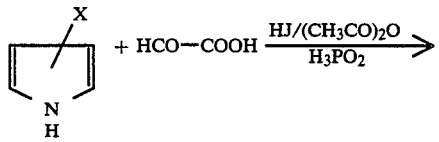

pyrrole (derivative)

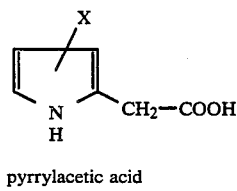

pyrrylacetic acid

In the endeavor to improve further the processes of the state of the art for the manufacture of p-hydroxyphenylacetic acid it has been proposed (German Offenlegungsschrift No. 2,944,480) to increase the economy of the process of catalytic hydrogenation of p-hydroxymandelic acid as described in German Offenlegungsschrift No. 2,820,854 (corresponding to Belgian Pat. No. 867,289) by carrying out said catalytic hydrogenation in an aqueous solution free from mineral acid, in particular free from hydrochloric acid. In this manner, practically the same yield as in German Offenlegungsschrift No. 2,820,854 (about 85%) is obtained, but corrosion and other problems resulting from the use of mineral acid are avoided.

It has further been found that p-hydroxymandelic acid can be reduced to p-hydroxyphenylacetic acid in excellent manner also with hydroiodic acid HI in the presence of red phosphorus.

The success of this reduction (with quantitative conversion of p-hydroxymandelic acid to p-hydroxyphenylacetic acid and yields of isolated product of up to about 95% of the theoretical) has been very surprising, especially with regard to the prejudice, created in European Offenlegungsschrift No. 3,825 and practically confirmed in German Offenlegungsschrift No. 2,820,854, against the possibility of a direct reduction of p-hydroxymandelic acid to p-hydroxyphenylacetic acid with the use of HI.

After having overcome this prejudice, the "one vessel" reaction known from Canad.J.Chem. 48, 139–143 (1970) for the heterocyclic series could be transferred to the manufacture of p-hydroxyphenylacetic acid.

It is, therefore, the object of the present invention to provide a process for the manufacture of p-hydroxyphenylacetic acid by reduction of p-hydroxymandelic acid, which comprises carrying out the reduction with HI in the presence of red phosphorus.

In the above process p-hydroxymandelic acid is used as such, as hydrate or in the form of its salts, preferably the alkali metal salts thereof and more preferably the sodium salt, or in the form of the hydrates thereof.

The reduction with HI and red phosphorus is carried out in the manner usual for such reductions, for example the conversion of unsubstituted mandelic acid into unsubstituted phenylacetic acid. It is possible, of course, to form the hydroiodic acid in the reduction mixture from one of its salts (for example KI) and an acid (for example phosphoric acid). According to a preferred embodiment, p-hydroxymandelic acid in aqueous hydroiodic acid is refluxed for a short period of time in contact with red phosphorus and the hydroiodic acid is subsequently recovered by distillation. In this case, the recovery of hydroiodic acid is almost quantitative.

When, instead of free p-hydroxymandelic acid, one of its salts is used, for example the sodium salt, the free hydroiodic acid can be recovered practically quantitatively.

The hot distillation residue is then diluted with water, unreacted phosphorus is separated by filtration of the hot solution and the filtrate is stirred until it has cooled to room temperature, whereupon p-hydroxyphenylacetic acid crystallizes in an especially pure form. By concentration of the mother liquor a further amount of reaction product can be obtained, so that a total yield of about 95% of the theoretical is obtained.

According to a preferred embodiment of the invention p-hydroxymandelic acid used as starting compound for the reaction is prepared in situ in a manner known per se (cf. for example Houben-Weyl, Methoden der organischen Chemie, volume VI/1c, pages 1057–1058 (1976)) from phenol and glyoxylic acid. By combining phenol and glyoxylic acid with hydroiodic acid in the presence of red phosphorus, the "one vessel" reaction directly yields p-hydroxyphenylacetic acid, without isolation of p-hydroxymandelic acid formed as intermediate. For this reaction phenol and glyoxylic acid should be used in a molar proportion of about 1:1. It proved advantageous, however, to use an excess amount of phenol, preferably about 1.3 mols for each mol of glyoxylic acid in order to suppress the formation of 2,4-dicarboxymethylphenol.

In this reaction, like in the normal mode of operation, hydrochloric acid is used as solvent, which can be recovered by distillation.

Phenol and glyoxylic acid react smoothly and with an almost quantitative conversion of the glyoxylic acid to give an isomer mixture consisting of about 85% of p- and about 15% of o-hydroxyphenylacetic acid. By crystallization in a manner analogous to that used in the normal mode of carrying out the process pure p-hydroxyphenylacetic acid is obtained in a yield of up to about 53%, calculated on the amount of glyoxylic acid used. Thus, the yield is in about the same order as in the two-stage reaction with isolation of p-hydroxymandelic acid. The "one vessel" mode operation according to the invention avoids the isolation of p-hydroxymandelic acid which is difficult because of the good solubility of this compound in water.

The hydroiodic acid used for the normal mode of carrying out the process of the invention and for the preferred embodiment can be used, in principle, in all possible solvents that are inert to the starting compounds and final products of the reaction, for example water or acetic acid. It is preferred to use aqueous hydroiodic acid, preferably hydroiodic acid of about 57% strength by weight having a constant boiling point at atmospheric pressure.

The glyoxylic acid used in the preferred embodiment is suitably used also in the form of an aqueous solution, preferably a commercial solution of about 50% strength by weight. The amount of water introduced into the reaction with the glyoxylic acid can be easily removed in the distillation of hydroiodic acid as first runnings. When the reaction is carried out in the same manner but with 80% by weight glyoxylic acid (glyoxylic acid monohydrate), hydroiodic acid can be recovered directly without first collecting the water.

The reaction is suitably carried out at a temperature in the range of from room temperature (about 20° C.) to about 150° C., temperatures between about room temperature and 100° C. being preferred.

As compared with the closest catalytic hydrogenation according to German Offenlegungsschrift No. 2,820,854 (yield 85%) and the process disclosed in German Offenlegungsschrift No. 2,944,480 (yield also about 85%) and in view of the fact that hydroiodic acid is used, the normal mode of operation of the the process of the invention constitutes a progressive or at least equivalent process because of the high yields obtained (up to about 95% of the theoretical), the high purity of the product and the simple recovery without much expense of the hydroiodic acid to be used. The chromium(II) salt method according to German Offenlegungsschrift No. 2,820 854 is less favorable because of the rather considerable problems of sewage pollution.

The progress over the process of European Offenlegungsschrift No. 3,825 resides in the fact that the detour via 3-chloro-4-hydroxymandelic acid can be avoided.

Moreover, the "one vessel" mode of execution of the process of the invention has the advantage of simplicity.

The following examples illustrate the invention.

EXAMPLE 1

10 kg of p-hydroxymandelic acid hydrate (53 mols), 34 kg (20 l) of 57% hydroiodic acid and 1.15 kg (37 mols) of red phosphorus are refluxed for 1 hour, whereupon the hydroiodic acid is distilled off at a sump temperature of up to 140° C. Further amounts of hydroiodic acid can be obtained from the distillation residue under a slight vacuum of 150 Torr. A total amount of 19.5 l of hydroiodic acid is recovered.

The distillation residue is diluted with 15 l of water and filtered off with suction while hot. In this manner 0.37 kg of red phosphorus are recovered.

The filtrate is stirred over-night until it has acquired room temperature, the precipitated p-hydroxyphenylacetic acid is filtered off with suction and washed with a small amount of water until it is free from iodine. After drying under reduced pressure at 80° C., 6.5 kg (80.6% of the theoretical) of product are obtained. Further amounts of p-hydroxyphenylacetic acid can be obtained by concentrating the mother liquor with subsequent crystallization as described above.

Total yield 7.76 kg or 95% of the theoretical, melting point 150° C.

EXAMPLE 2

75 kg of sodium salt hydrate of p-hydroxymandelic acid (360 mols), 260 kg of 57% hydroiodic acid and 7.5 kg of red phosphorus (242 mols) are refluxed for 1 hour. Over a packed column about 28 l of water are distilled off as first runnings at a reflux ratio of 2:1. Under the conditions specified in Example 1, 168 kg of re-usable hydroiodic acid are distilled off.

The distillation residue is diluted with 155 l of water and worked up as described in Example 1. Yield 52 kg of p-hydroxyphenylacetic acid or 95% of the theoretical, melting point 150° C.

EXAMPLE 3

1.48 kg of 50% aqueous glyoxylic acid (10 mols) are added dropwise, over a period of 2 hours at 25° C., to a thoroughly stirred mixture of 1.22 kg of phenol (13 mols), 190 g of red phosphorus (6.1 mols) and 4 l (6.8 kg) of 57% hydroiodic acid and stirring is continued over-night at 25° C.

The reaction mixture is then heated for 1 hour to 90° C., whereupon about 650 g of a phenol/water azeotrope is distilled off as first runnings at 150 Torr over a packed column at a reflux ratio of 2:1.

Next, 6.8 kg of phenol-containing hydroiodic acid pass over, which is re-used in the following reactions. The hot distillation residue is diluted with 3 l of water, unreacted red phosphorus is filtered off with suction and the filtrate is stirred until the temperature has dropped to 5° C. The precipitated p-hydroxyphenylacetic acid is filtered off with suction, washed three times with 400 ml of water each until it is free from iodine and dried at 80° C. under reduced pressure. Yield 741 g or 48.8% of the theoretical.

When in the following reactions, the wash water of p-hydroxyphenylacetic acid is used to dilute the distillation residue, the yield is increased to 811 g of p-hydroxyphenylacetic acid or 53.4% of the theoretical, melting point 150° C.

What is claimed is:

1. A one-step process for the direct manufacture of p-hydroxyphenyl-acetic acid consisting essentially of reducing unsubstituted p-hydroxymandelic acid in an aqueous hydroiodic acid solvent with HI in the presence of red phosphorous and recovering precipitated p-hydroxyphenylacetic acid.

2. The process of claim 1, wherein said aqueous solution is about 57% by weight aqueous hydroiodic acid having a constant boiling point.

3. The process of claim 1, wherein the p-hydroxymandelic acid is prepared in situ by combining phenol and glyoxylic acid.

4. The process of claim 3, wherein said glyoxylic acid is in the form of a commercial aqueous solution of about 50% by weight.

* * * * *